(12) United States Patent
Deisseroth

(10) Patent No.: US 9,889,188 B1
(45) Date of Patent: Feb. 13, 2018

(54) EBOLA VIRUS COMPOSITION/VACCINE

(71) Applicant: Albert B. Deisseroth, Potomac, MD (US)

(72) Inventor: Albert B. Deisseroth, Potomac, MD (US)

(73) Assignee: MICROVAX, LLC, Warrenton, VA (US)

( * ) Notice: Subject to any disclaimer, the term of this patent is extended or adjusted under 35 U.S.C. 154(b) by 0 days.

(21) Appl. No.: 15/341,389

(22) Filed: Nov. 2, 2016

Related U.S. Application Data

(60) Provisional application No. 62/249,975, filed on Nov. 3, 2015.

(51) Int. Cl.

| | | |
|---|---|---|
| *A61K 39/395* | (2006.01) |
| *C07K 16/28* | (2006.01) |
| *C07K 16/00* | (2006.01) |
| *G01N 33/53* | (2006.01) |
| *A61K 45/06* | (2006.01) |
| *A61K 39/12* | (2006.01) |
| *C12N 7/00* | (2006.01) |
| *C07K 14/005* | (2006.01) |
| *C07K 14/705* | (2006.01) |
| *A61K 39/00* | (2006.01) |

(52) U.S. Cl.
CPC ............ *A61K 39/12* (2013.01); *C07K 14/005* (2013.01); *C07K 14/70575* (2013.01); *C12N 7/00* (2013.01); *A61K 2039/5256* (2013.01); *A61K 2039/53* (2013.01); *A61K 2039/54* (2013.01); *A61K 2039/57* (2013.01); *A61K 2039/575* (2013.01); *C07K 2319/40* (2013.01); *C12N 2710/10043* (2013.01); *C12N 2760/14122* (2013.01); *C12N 2760/14134* (2013.01); *C12N 2760/14171* (2013.01)

(58) Field of Classification Search
CPC .......... A61K 2300/00; A61K 2039/505; A61K 45/06; C07K 2317/76; C07K 2317/21
See application file for complete search history.

*Primary Examiner* — Barry A. Chestnut
(74) *Attorney, Agent, or Firm* — Jacob Frank; Glenn Snyder

(57) ABSTRACT

The present invention is directed to a composition and/or plasmid and/or vector vaccine which encodes four fragments of the GP1 Ebola protein attached to the extracellular domain of the potent immunostimulatory protein CD40 ligand, in the configuration of two compositions and/or vaccines that are mixed together, to respectively increase the levels of antibodies and CD8 effector T cells, against the lethal Ebola virus.

10 Claims, 1 Drawing Sheet

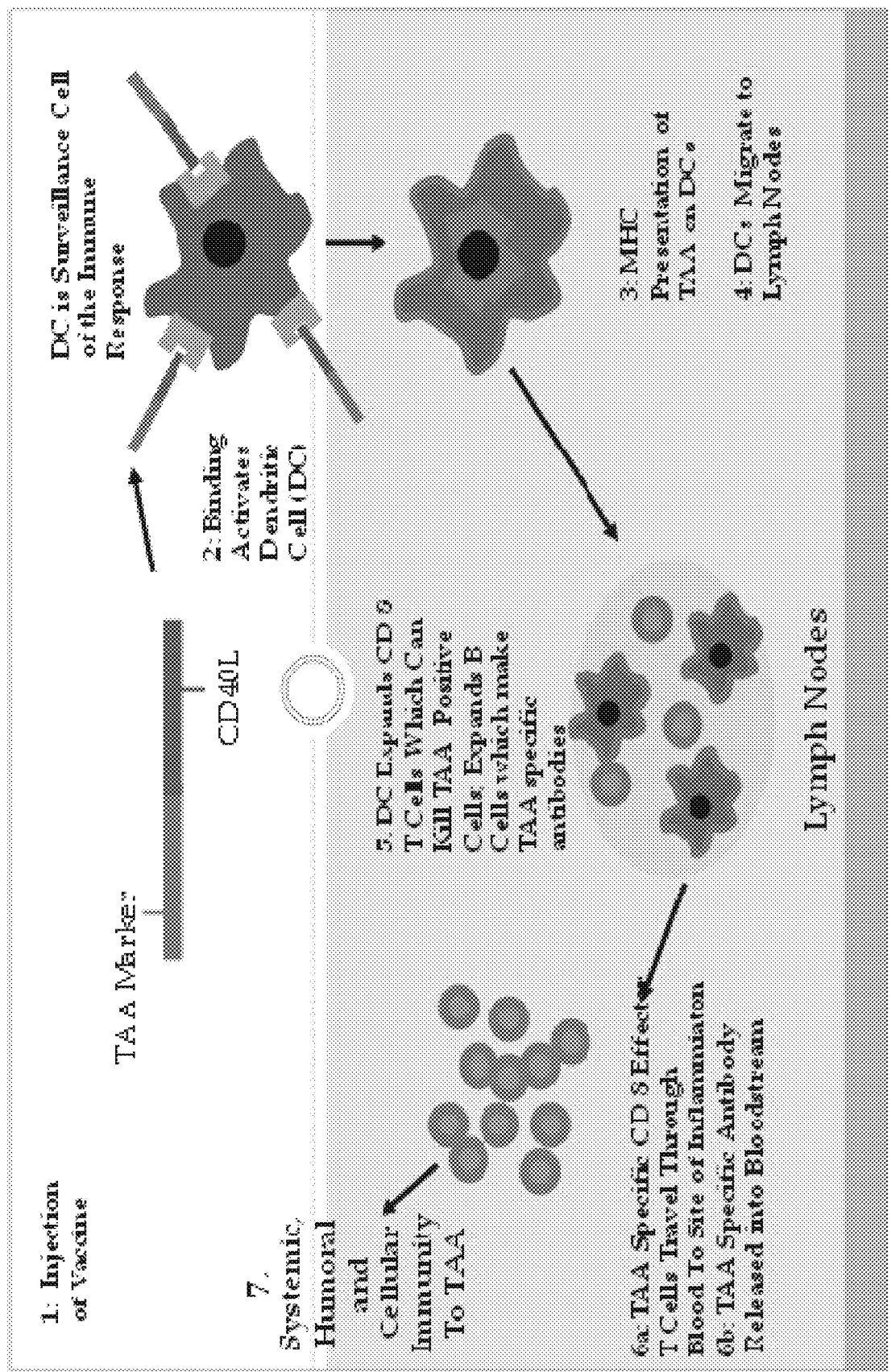

EBOLA VIRUS COMPOSITION/VACCINE

CROSS-REFERENCE TO RELATED APPLICATIONS

This application claims priority and the benefit under 35 U.S.C. 119(e) of U.S. Provisional Patent Application Ser. No. 62/249,975, filed on Nov. 3, 2015, the disclosure of which is hereby incorporated by reference herein.

FIELD OF THE INVENTION

The present invention relates generally to the field of Ebola virus infection, and more specifically, to novel compositions and/or vaccine which includes selected fragments of the GP1 protein fused to the CD40 ligand, for acting against the Ebola virus infections.

BACKGROUND OF THE INVENTION

Background Information on Ebola:

Infected individuals usually present with the onset of fever, chills, myalgias, 2-21 days following exposure to other infected individuals which is followed by multi-organ failure associated with disruption of the endothelial surface of vessels (1), release of cytokines systemically (1), and induction of disseminated intravascular coagulation (2) which leads to death of 50% of the infected individuals in areas of the world where the comprehensive support of individuals with multi-organ failure is difficult. The single negative strand RNA of Ebola encodes a number of whole proteins, some of which suppress the adaptive immune response and others, like GP1, mediates attachment and uptake of the virus into host cells (3-4).

The Ebola virus genome has seven genes, NP, VP35, VP40, GP, VP30, VP24, and L (8). The GP gene encodes two proteins, a secreted form called sGP, and a transmembrane form called GP which is produced by RNA editing (8). GP is synthesized as a single polypeptide of 676 amino acids in length (8). A cleaved GP (GPO), is further cleaved by a cellular protease into a surface subunit GP1 and GP2. The GP1 subunit is responsible for receptor binding, and GP2 mediates virus-cell membrane fusion and viral entry (8).

Available Vaccines:

Up to the present time, the use of inactivated viral strains, other viruses which have been pseudotyped for Ebola proteins, plasmid expression vectors encoding the GP1 protein, and the plasmid prime being boosted with an adenoviral vector encoding the GP1 protein, have been studied (1).

A New Direction for Ebola Vaccine.

A cDNA vaccine which encodes several selected fragments of the GP1 Ebola protein are proposed to be selectively attached to the extracellular domain (ecd) of the potent immunostimulatory protein CD40 ligand (CD40L) in order to increase the levels of antibodies which will protect mice against a lethal challenge of the mouse adapted Zaire strain of the Ebola virus, or the levels off neutralizing antibodies which are induced to that mouse adapted Zaire Ebola virus.

Definitions

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context.

As used herein, the terms "antigen" or "antigenic factors" refers broadly to any antigen to which a human, mammal, bird or other animal can generate an immune response. The terms "antigen" or "antigenic factors" as used herein refers broadly to a molecule that contains at least one antigenic determinant to which the immune response may be directed. The immune response may be cell-mediated, humoral or both. As is well known in the art, an antigen may be protein, carbohydrate, lipid, or nucleic acid or any combinations of these biomolecules. As is also well known in the art, an antigen may be native, recombinant or synthetic. For example, an antigen may include non-natural molecules such as polymers and the like. Antigens include both self-antigens and non-self antigens. As used herein, "antigenic determinant" (or epitope) refers to a single antigenic site on an antigen or antigenic factor; it is a minimal portion of a molecule that recognized by the immune system, specifically by antibodies, B cells or T cells. Antigenic determinants may be linear or discontinuous.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" with reference to administering the fusion protein or an expression vector encoding that protein, is an amount that results in an increase in the immune response as measured by an increase in T cell activity and/or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr[1]]-MDP (Byersand Allison, *Vaccine* 5:223 (1987)), monophosphoryl lipid A (Johnson et al., *Rev. Infect. Dis.* 9:S512 (198)), and the like.

The term "vector" as used in this application contains a transcription unit (also known as an "expression vector"). It encompasses both viral and non-viral expression vectors that when administered in vivo can enter target cells and express an encoded protein. Viral vectors have evolved means to overcome cellular barriers and immune defense mechanisms. Viral vectors suitable for in vivo delivery and expression of an exogenous protein are well known in the art and include adenoviral vectors, adeno-associated viral vectors, retroviral vectors, vaccinia vectors, pox vectors, herpes simplex viral vectors, etc. Viral vectors are preferably made replication defective in normal cells. For example, see U.S. Pat. Nos. 6,669,942; 6,566,128; 6,794,188; 6,110,744 and 6,133,029. On the other hand, non-viral gene carriers consistently exhibit significantly reduced transfection efficiency as they are hindered by numerous extra- and intracellular obstacles. Non-viral vectors for gene delivery comprise various types of expression vectors (e.g., plasmids) which are combined with lipids, proteins and other molecules (or combinations of thereof) in order to protect the DNA of the vector during delivery. Fusigenic non-viral particles can be constructed by combining viral fusion proteins with expression vectors as described. Kaneda, *Curr Drug Targets* (2003) 4(8):599-602. Reconstituted HVJ (hemagglutinating virus of Japan; Sendai virus)-liposomes can be used to deliver expression vectors or the vectors may be incorporated directly into inactivated HVJ particles without liposomes. See Kaneda, *Curr Drug Targets* (2003) 4(8):599-602. DMRIE/DOPE lipid mixture is useful as a vehicle for non-viral expression vectors. See U.S. Pat. No. 6,147,055. Polycation-DNA complexes also may be used as a non-viral gene delivery vehicle. See Thomas et al., *Appl Microbiol Biotechnol* (2003) 62(1):27-34. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector is preferably administered subcutaneously.

The term "transcription unit" as used herein with connection to an expression vector means a stretch of DNA that is transcribed as a single, continuous mRNA strand by RNA polymerase, and includes the signals for initiation and termination of transcription. For example, in one embodiment, a transcription unit of the invention may include nucleic acid that encodes from 5' to 3' a secretory signal sequence, an GP1 antigen fragment and CD40 ligand. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "secretory signal sequence" (also known as "signal sequence," "signal peptide," leader sequence," or leader peptide") as used herein refers to a short peptide sequence, generally hydrophobic in charter, including about 20 to 30 amino acids that is synthesized at the N-terminus of a polypeptide and directs the polypeptide to the endoplasmic reticulum. The secretory signal sequence is generally cleaved upon translocation of the polypeptide into the endoplasmic reticulum. Eukaryotic secretory signal sequences are preferred for directing secretion of the exogenous gene product of the expression vector. A variety of suitable such sequences are well known in the art and include the secretory signal sequence of human growth hormone, immunoglobulin kappa chain, and the like. In some embodiments, the endogenous tumor antigen signal sequence also may be used to direct secretion.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that defend a cell from an antigen or infectious body by neutralizing any effect it has biologically.

The term "linker" as used employed in this application with respect to the transcription unit of the expression vector refers to one or more amino acid residues between the carboxy terminal end of the antigen and the amino terminal end of CD40 ligand. The composition and length of the linker may be determined in accordance with methods well known in the art and may be tested for efficacy. (See, e.g. Arai et al. *Protein Engineering*, Vol. 4, No. 8, 529-532, August 2001). In certain embodiments of the present invention, the linker is from about 3 to about 15 amino acids long, more preferably from about 5 to about 10 amino acids long. However, longer or shorter linkers may be used or the linker may not be used at all. Longer linkers may be up to about 50 amino acids, or up to about 100 amino acids. One example of a linker well known in the art is a 15 amino acid linker consisting of three repeats of four glycines and a serine (i.e., [Gly$_4$Ser$_3$)].

BRIEF DESCRIPTION OF THE DRAWING

FIG. 1 illustrates an overview of TAA/ecdCD40L vaccine platform for application in infectious diseases, in which a fragment of the target associated antigen (TAA) is attached to extracellular domain (ecd) of the potent immunostimulatory antigen CD40L.

DETAILED DESCRIPTION OF THE INVENTION

Location of Amino Acid Fragments of the Ebola GP1 Protein Proposed for Ebola Composition and/or Vaccine.

Fragments Which Bind Antibodies Which Protect Mice Against Lethal Challenge with a Mouse Adapted Ebola Zaire Virus: Wilson et al (5) identified the three lines peptides from GP1 which bound to antibodies which protected two strains of mice (BALB/c and C57BL/6) from a lethal challenge by the Zaire strain of Ebola virus:

a. Peptide 1: AA 401-417 (SEQ ID No. 1-ATQVEQHHRRTDNDSTA)

b. Peptide 2: AA 389-405 (SEQ ID NO. 2-HNTPVYKLDISEATQVE)

c. Peptide 3: AA 477-493 (SEQ ID NO. 3-GKLGLITNTIAGVAGLI)

These three peptides primarily bind antibodies and are from the same GP1 protein, and they are each relatively short (each approximately 16 amino acids in length). These three peptides are fused together with ecdCD40L as part of a first composition and/or vaccine, whereas SEQ ID NO 4 (addressed below) is separately fused with ecdCD40L as a second composition and/or vaccine which is a relatively long amino acid listing of 60 amino acids which primarily contains contact sites for the cellular receptor.

The amino acids, for example, in bold font in SEQ ID NO. 1 are considered the most important component of each peptide for binding to the protective antibodies. Each of the antibodies binding these peptides would protect mice from a lethal Ebola challenge when 100 micrograms of the antibody were administered 24 hours before challenge. The percentage of mice protected decreased as the dose of antibody was decreased to 25 micrograms. The antibody binding to peptide 2 (SEQ ID NO. 2) neutralized the infectivity of Ebola whereas the antibodies binding to peptides 1 and 3 (SEQ ID NOS. 1 and 3) did not. Although the antibodies binding to peptides 1-3 (SEQ ID NO. 1-SEQ ID NO.3) bound GP1 from both Ebola strains from Zaire, they did not bind Ebola strains from the Ivory Coast nor from Sudan. The region of GP1 from which these 3 peptides are derived is poorly conserved among Ebola strains and are not shared by any region in the soluble form of GP1. On the basis of these peptides being recognized by neutralizing antibodies to Ebola, the peptides 1-3 (SEQ ID NO. 1-SEQ ID NO. 3) are proposed to be attached to ecdCD40L to generate Composition and/or Vaccine 1.

Fragment from the Region of Ebola GP1 which Contains Contact Sites for the Cellular Receptor:

The amino acid regions between amino acids 54-201 has been shown to contain the "base and head" regions of GP1 which are thought to play a role in attachment of the Ebola virus to its cellular receptors (6-9). Amino acid residues K114, K115, K140, G 143, P146 and C147 have been proposed as important contact sites for the GP1 with its cellular receptor (6). All the amino acids in the proposed receptor binding region (AA 54-201) are highly conserved among all Ebola strains (6). Therefore, the amino acids between AA100 and AA160 (see reference 8) are proposed as the fourth peptide (SEQ ID NO. 4 below) to attach to ecdCD40L to generate Composition and/or Vaccine II. As noted above the composition and/or second vaccine II is distinct in its structure from the first composition and/or vaccine in that the first composition and/or vaccine comprises the three peptides comprising SEQ ID NOS 1-3. A mixture of these two vaccines/compositions I and II, would serve as the composition and/or vaccine, for individuals infected with and/or to prevent being infected with, the Ebola virus. Although not wishing to be bound by any theory, it is believed that the cells infected in the vicinity of the site of injection, the antigen/CD40 ligand secretory which is taken up by antigen presenting cells (e.g. DCs) in the vicinity of the infected cells would be that the fewer the compositions and/or vaccines mixed would enhance the injected particles to be taken up and connect to the CD40 port on dendritic cells.

AA100-AA160 of GP1: (EAGEWAENCYNLEIKKPDG-SECLPAAPDGIRGFPRCRYVHKVSGTGPCAGGFAFH-KEG AFF-SEQ ID NO. 4)

TAA/ecdCD40L Composition and/or Vaccine Induces High Titers of Neutralizing Antibodies.

Applicant has developed a TAA/ecdCD40L vaccine platform, as illustrated in FIG. 1, for application in infectious diseases, in which a fragment of the target associated antigen (TAA) is attached to extracellular domain (ecd) of the potent immunostimulatory antigen CD40L (10-14). The attachment of the TAA to the ecdCD40L is designed to promote presentation of TAA on Class I as well as Class II MHC and provide helper function thereby overcoming the defective response to vaccination in immunosuppressed, debilitated patients including those who are of advanced chronological age, and increasing the potency of antigens which are weak immunogens to increase the titer of neutralizing antibodies induced by the vaccine (10-14). The TAA needs to be sufficiently small so that it does not disrupt the natural assembly of a homotrimeric array trimeric of the native wild type CD40 ligand. The fusion protein is engineered to be secreted from vector infected cells by the addition of a signal sequence to the amino terminal end of the TAA protein and by deletion of the transmembrane and preferably cytoplasmic domains of the CD40 ligand. The TAA/ecdCD40L composition and/or vaccine platform has shown to induce robust immune responses against 7 different antigenic targets associated with both cancer cells as well as infectious agents. A phase I clinical trial of a TAA/ecdCD40L cancer vaccine is currently under way (14). A fusion protein vaccine comprised of 2 fragments from the region of the H5N1 influenza hemagglutinin protein which binds cellular receptors attached to the ecdCD40L induced neutralizing antibody titers for influenza virus of over 1/4500 (13). The robustness of both the humoral as well as the cellular immune response induced by the TAA/ecdCD40L vaccine platform, as well as the high titers of neutralizing antibodies induced against foreign antigens on infectious agents, suggest that a TAA/ecdCD40L composition and/or vaccine which targets epitopes in the GP1 glycoprotein would be valuable both to prevent infection as well as reduce the tissue damage and mortality of individuals already infected with Ebola.

TAA/ecdCD40L Composition and/or Vaccine for Ebola.

For Composition/Vaccine #1, we will construct 2 expression plasmid cDNA transcription units, one comprised of a CMV promoter linked to a secretory sequence (sig) which is linked to the following three fragments (SEQ NOS 1-3) of the Ebola GP1 protein (which were described above in Section 4) attached to a 9 AA linker which is attached to the ecdCD40L: For Composition/Vaccine #2, a second expression plasmid cDNA transcription unit would be comprised of a CMV promotor linked to a secretory sequence (sig) which is linked to the fragment SEQ ID NO. 4 of the GP1 protein a. Peptide 1: AA 401-417 (SEQ ID NO. 1)
b. Peptide 2: AA 389-405 (SEQ ID NO. 2)
c. Peptide 3: AA 477-493 (SEQ ID NO. 3)
d. Peptide 4: AA 100-160 (SEQ ID NO. 4)

The plasmid expression vectors which encodes each of the two fusion proteins generated by attachment of each one of these peptides to the ecdCD40L will be designated as follows:

a. Composition and/or Vaccine I: pEbolaGP1$_{401-417}$/ecdCD40L, and pEbolaGP1$_{389-405}$/ecdCD40L, and pEbolaGP1$_{477-493}$/ecdCD40L b. Composition and/or Vaccine II: pEbolaGP1$_{100-160}$/ecdCD40L These two plasmid expression vectors will be employed by administration intramuscularly (IM) as a 1:1 mixture of these two plasmids on Days 1, 7 and 21. The employment of these two plasmid compositions and/or vaccines could establish the ability of the TAA/ecdCD40L platform as an effective immunotherapeutic solution for the Ebola virus.

Summary of Advantages of TAA/ecdCD40L Composition/Vaccine:

Based on the pre-clinical studies of the TAA/ecdCD40L in TAA transgenic mouse models, the following advantages can be identified for the TAA/ecdCD40L vaccine strategy as compared to existing vaccine strategies:

1. The TAA/ecdCD40L composition/vaccine only requires 3 weeks to administer in order to induce a potent response due to the linkage to the ecdCD40L, thereby making it useful for use in containment of outbreaks in a local geographical area;
2. TAA/ecdCD40L overcomes anergy that may arise in patients with chronic disease (10, 12);

3. TAA/ecdCD40L induces higher titers of which are either protective or neutralizing;
4. The safety concerns with the attenuated Ebola vaccine strains will not exist with the TAA/ecdCD40L vaccine proposed above;
5. The vaccine would work better in older subjects (greater than 55 years) in which age group vaccines do not induce a fully protective immune response (12);
6. Two vector injections produce a memory response for at least a year (10);
7. Vector vaccine stable when frozen for up to 7 years.

9. REFERENCES

1. Sullivan N, Yang Z Y, and Nabel G J. Ebola virus pethogenesis: implications for vaccines and therapies. Journal of Virology 77: 9733-9737, 2003.
2. Geisbert T W, Young H A, Jahrling P B, Davis K J, Kagan E and Hensley L E. Mechanisms underlying coagulation abnormalities in Ebola hemorrhagic fever. Journal of Infectious Diseases 188: 1618-1629, 2003.
3. Mercer J, and Helenius A. Virus entry by macropinocytosis. Nature Cell Biology 11: 510-520, 2009.
4. Francica J R, Varela-Rohena A, Medvec A, Plesa G, Riley J L, and Bates P. Steric shielding of surface epitopes and impaired immune recognition induced by the Ebola virus glycoprotein. PLoS Pathogens 6: e1001098, 2010.
5. Wilson J A, Hevey M, Biken R, Guest S, Bray M, Schmaljohn A L, and Hart M K. Epitopes involved in antibody-mediated protection from Ebola virus. Science 287: 1664-1666, 2000.
6. Lee J L, Fusco M L, Hessell A J, Oswald W B, Burton D R, and Saphire E O. Structure of the Ebola virus glycoprotein bound to a human survivor antibody. Nature 454:177-182, 2008.
7. Brindley M A et al. Ebola virus glycoprotein I: identification of residues important for binding and post binding events. Journal of Virology 81: 7702-7709, 2007.
8. Manicassamy B, Wang J, Jiang H. and Rong L. Comprehensive analysis of Ebola virus GP1 in viral entry. Journal of Virology 79: 4793-4805, 2005.
9. Mpanju O M, Towner J S, Dover J E, Nichol St, Wilson C A. Identification of two amino acid residues on Ebola virus gloprotein 1 critical for cell entry. Virus Research 121: 205-214, 2006.
10. Zhang L, Tang Y, and Deisseroth A: Adenoviral vectors encoding a secretable HPV 16 E7/CD40 ligand fusion protein induce immunity for up to one year in a murine model. *PNAS,* 100: 15101-15106, 2003.
11. Tang, Y, Zhang, L, Yuan, J, Maynard, J, and Deisseroth, A. Multi-step process of vector mediated activation and tumor antigen loading of APC by CD40 ligand/tumor antigen secretory protein generates protection from cancer cell lines. *Blood,* 104: 2704-2713, 2004.
12. Tang, Y C, Maynard J, Akbulut H, Fang X M, Zhang W W, Xia X Q, Koziol J, Linton P J, and Deisseroth A. Vector Prime/Protein Boost Vaccine Which Overcomes Defects Acquired During Aging and Cancer. *J. Immunology,* 177:5697-5707, 2006.
13. Tang, Y C, Linton, P J, Thoman M, and Deisseroth A. Symposium in Writing: Vaccine for Infections and Cancer. *Cancer Immunology Immunotherapy* 58: 1949-1957, 2009.
14. Deisseroth A, Tang Y C, Zhang L, Akbulut H, and Habib N. TAA/ecdCD40L adenoviral prime-protein boost vaccine for cancer and infectious diseases. *Cancer Gene Therapy* 20: 65-69, 2013.

The invention claimed is:

1. A pharmaceutical composition comprising a mixture of at least two vectors for generating a humoral and cellular response against an Ebola virus in an individual, comprising:
   a first expression vector containing a first transcription unit encoding a first fusion protein comprising (a) three fragments SEQ ID NOS 1-3, (b) a first extracellular domain of a secretable CD40 ligand, (c) a linker connecting said three fragments to an amino terminal end of the extracellular domain of the secretable CD40 ligand;
   a second expression vector containing a second transcription unit encoding a second fusion protein comprising (a) a single fragment SEQ ID NO. 4, (b) a second extracellular domain of a secretable CD40 ligand, (c) a linker connecting said single fragment to an amino terminal end of the extracellular domain of the second CD40 ligand; and
   said first and second fusion proteins each configured for promoting an antibody response against the Ebola virus and a CD8 effector T cell response against the Ebola virus.

2. A pharmaceutical composition of claim 1, wherein said fragments are all from the protein pEbolaGP1.

3. A pharmaceutical composition of claim 1, wherein said composition is subcutaneously administered as a single dose or as multiple doses.

4. A pharmaceutical composition of claim 1, wherein said expression vector is a plasmid DNA or viral vector.

5. The composition of claim 1, wherein said expression vector is an adenoviral vector.

6. The composition of claim 1, wherein the size of said single fragment or said three fragments each linked to an extracellular domain of the CD40 ligand, is sufficiently small so as not to disrupt the assembly of the CD40L trimer.

7. The composition of claim 1, wherein the CD40 ligand is a human CD40 ligand.

8. The composition of claim 1, wherein each of said three fragments SEQ ID NOS. 1-3, has an epitope recognized and bound by Class I and Class II MHC, and said one fragment SEQ ID NO. 4 has an epitope recognized and bound by Class I MHC and Class II MHC.

9. The composition of claim 1, wherein said antibody response is a neutralizing antibody response.

10. A method to help protect an individual against the Ebola virus by administering to the individual one or more pharmaceutical compositions of claim 1.

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Synthetic Construct

<400> SEQUENCE: 1

Ala Thr Gln Val Glu Gln His His Arg Arg Thr Asp Asn Asp Ser Thr
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

His Asn Thr Pro Val Tyr Lys Leu Asp Ile Ser Glu Ala Thr Gln Val
1               5                   10                  15

Glu

<210> SEQ ID NO 3
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 3

Gly Lys Leu Gly Leu Ile Thr Asn Thr Ile Ala Gly Val Ala Gly Leu
1               5                   10                  15

Ile

<210> SEQ ID NO 4
<211> LENGTH: 61
<212> TYPE: PRT
<213> ORGANISM: Artificial Sequence
<220> FEATURE:
<223> OTHER INFORMATION: Synthetic Construct

<400> SEQUENCE: 4

Glu Ala Gly Glu Trp Ala Glu Asn Cys Tyr Asn Leu Glu Ile Lys Lys
1               5                   10                  15

Pro Asp Gly Ser Glu Cys Leu Pro Ala Ala Pro Asp Gly Ile Arg Gly
                20                  25                  30

Phe Pro Arg Cys Arg Tyr Val His Lys Val Ser Gly Thr Gly Pro Cys
            35                  40                  45

Ala Gly Gly Phe Ala Phe His Lys Glu Gly Ala Phe Phe
        50                  55                  60
```